US008859824B2

(12) United States Patent
Walter et al.

(10) Patent No.: US 8,859,824 B2
(45) Date of Patent: Oct. 14, 2014

(54) DUAL CATION DUAL ANION COORDINATION COMPLEXES

(75) Inventors: Mary Ann Walter, La Vernia, TX (US); Jian Gao, Helotes, TX (US); Neill Bailey Walsdorf, San Antonio, CA (US)

(73) Assignee: Mission Pharmacal Company, San Antonio, TX (US)

(*) Notice: Subject to any disclaimer, the term of this patent is extended or adjusted under 35 U.S.C. 154(b) by 799 days.

(21) Appl. No.: 12/651,927

(22) Filed: Jan. 4, 2010

(65) Prior Publication Data

US 2010/0184866 A1  Jul. 22, 2010

Related U.S. Application Data

(60) Provisional application No. 61/146,572, filed on Jan. 22, 2009.

(51) Int. Cl.
| | | |
|---|---|---|
| *C07C 43/30* | (2006.01) | |
| *A61K 31/075* | (2006.01) | |
| *A61K 31/19* | (2006.01) | |
| *A61K 31/194* | (2006.01) | |
| *C07C 59/265* | (2006.01) | |

(52) U.S. Cl.
CPC ............. *A61K 31/194* (2013.01); *C07C 59/265* (2013.01)
USPC ............................ 568/591; 514/715; 514/574

(58) Field of Classification Search
CPC ..... A61K 31/075; A61K 31/08; A61K 31/16; A61K 31/19; A61K 31/194; A61K 8/362; A61K 31/195; A01N 31/04; A61Q 19/00; C07C 43/132; C07C 43/315; C07C 403/10; C07C 41/56; C07C 43/30; C07C 45/515
USPC .................................. 514/715, 574; 568/591
See application file for complete search history.

(56) References Cited

U.S. PATENT DOCUMENTS

| | | | |
|---|---|---|---|
| 4,556,561 A | 12/1985 | Brown et al. | |
| 4,895,980 A * | 1/1990 | Walsdorf | ........................ 562/584 |
| 4,985,593 A | 1/1991 | Walsdorf et al. | |
| 5,075,499 A * | 12/1991 | Walsdorf et al. | ............... 562/590 |
| 5,219,889 A | 6/1993 | Walsdorf et al. | |
| 5,228,445 A | 7/1993 | Pak | |
| 5,432,200 A | 7/1995 | Walsdorf et al. | |
| 6,287,607 B2 | 9/2001 | Pak et al. | |
| 6,485,708 B1 | 11/2002 | Winston et al. | |
| 7,091,246 B2 | 8/2006 | Rushforth | |

FOREIGN PATENT DOCUMENTS

| | | |
|---|---|---|
| EP | 0673913 A1 | 9/1995 |
| FR | 2451 M | 3/1963 |
| WO | WO2005087218 | 9/2005 |

OTHER PUBLICATIONS

Ruml et al.; "The Effect of Varying Molar Ratios of Potassium-Magnesium Citrate on Thiaide-lnduced Hypokalemia and Magnesium Loss"; 1998; J. Clin. Pharmacol.; 38:1035-1041.*

Ruml et al. J. Clin Pharmcol (1998); 38; 1035-1041 (already of record).*
Antich et al. (1993) "Measurement of Intrinsic Bone Quality In Vivo by Reflection Ultrasound: Correction of Impaired Quality with Slow-Release Sodium Fluoride and Calcium Citrate," *J. Bone Miner. Res.* 8(3):301-311.
Caverzasio et al. (Jun. 1998) "Fluoride: Mode of Action," *Bone* 22(6):585-589.
Fatemi et al. (1991) "Effect of Experimental Human Magnesium Depletion on Parathyroid Hormone Secretion and 1,25-Dihydroxyvitamin D Metabolism," *Clin. Endocrinol. Metab.* 73(5):1067-1072.
Johnston et al. (Jul. 9, 1992) "Calcium Supplementation and Increases in Bone Mineral Density in Children," *N Engle. J. Med.* 327(2):82-87.
King et al. (1991) "The Effect of In Ovo Boron Supplementation on Bone Mineralization of the Vitamin D-Deficient Chicken Embryo," *Biolog. Tace Elem. Res.* 31:223-233.
Koenig et al. (Feb. 1991) "Bioavailability of Potassium and Magnesium, and Citraturic Response from Potassium-Magnesium Citrate," *J. Urol.* 145:330-334.
Lehmann et al. (Mar. 1998) "Drinking Water Fluoridation: Bone Mineral Density and Hip Fracture Incidence," *Bone* 22(3):273-278.
Luisi et al. (Jun. 8, 2007) "Coordination Polymer Gels: Synthesis, Structure and Mechanical Properties of Amorphous Coordination Polymers," *Chem. Commun.* :2802-2804.
Mertz, W. (Sep. 18, 1981) "The Essential Trace Elements," *Science* 213:1332-1338.
Meunier et al. (Jan. 29, 2004) "The Effects of Strontium Ranelate on the Risk of Vertebral Fracture in Women with Postmenopausal Osteoporosis," *N. Engl. J. Med.* 350(5):459-468.
Oh et al. (Dec. 1, 2005) "Chemically Tailorable Colloidal Particles from Infinite Coordination Polymers," *Nature* 438:651-654.
Pak et al. (Sep. 15, 1995) "Treatment of Postmenopausal Osteoporosis with Slow-Release Sodium Fluoride," *Ann. Intern. Med.* 123(6):401-408.
Pak et al. (1989) "Safe and Effective Treatment of Osteoporosis with Intermittent Slow Release Sodium Fluoride: Augmentation of Vertebral Bone Mass and Inhibition of Fractures," *J. Clin. Endocrinol. Met.* 68(1):150-158.

(Continued)

*Primary Examiner* — Shirley V Gembeh
(74) *Attorney, Agent, or Firm* — Ellen P. Winner

(57) ABSTRACT

Compounds are provided herein which are coordination complexes of the formula, $A_xB_yCit_2F_z \cdot mH_2O$, wherein A is a cation selected from certain IA or IIA metal ions in the Periodic Table; B is a cation selected from certain IIA metal ions and certain divalent d-block transition metal ions; A and B are different; "Cit" is tribasic citric acid anion; the stoichiometric ratio of x to y is equal or higher than 1.0 but lower than 8.0; m is 0-12; and z is selected such that electroneutrality is preserved. Compounds provided herein are useful to treat dietary deficiencies, osteoporosis, osteopenia, bone loss, and risk of bone loss, as well as other medical conditions involving the need for administration of the various ions. In addition, the compounds can be used as fluoride sources for dental use and to fluoridate water systems.

5 Claims, 19 Drawing Sheets

(56) References Cited

OTHER PUBLICATIONS

Strause et al. (1994) "Spinal Bone Loss in Postmenopausal Women Supplemented with Calcium and Trace Minerals," *Calc. Trace Miner. Bone Dens.* 124:1060-1064.

Tang et al. (2004) "Biological Modification in the Brushite Crystallization," *Mater. Res. Soc. Symp. Proc.* 823:81-89.

Vescini et al. (2005) "Long-Term Potassium Citrate Therapy and Bone Mineral Density in Idiopathic Calcium Stone Formers," *J. Endocrinol. Invest.* 28:218-222.

Wikipedia, *Coordination Polymers*, Downloaded Jul. 14, 2008.

Zerwekh et al. (1997) "The Effect of Intermittent Slow-Release Sodium Fluoride and Continuous Calcium Citrate Therapy on Calcitropic Hormones, Biochemical Markers of Bone Metabolism, and Blood Chemistry in Postmenopausal Osteoporosis," *Calcif. Tissue Int.* 61:272-278.

International Search Report and Written Opinion for corresponding PCT Application No. PCT/US10/20048, dated Mar. 1, 2010.

\* cited by examiner

DUAL CATION DUAL ANION COORDINATION COMPLEXES

CROSS-REFERENCE TO RELATED APPLICATIONS

This application claims the benefit of U.S. Provisional Application No. 61/146,572, filed Jan. 22, 2009, which application is incorporated by reference in its entirety to the extent there is no inconsistency with the present disclosure.

BACKGROUND

It is well known that a number of nutrients are critically important in bone health. Fluoride is an essential trace element (see Mertz, W. Science, 1981) with potent anabolic activity in bone (Caverzasio, J. et al., Bone, 1998). A number of cations are useful to promote bone health, as follows.

Calcium is the main bone-forming mineral (see Johnston, C. C. et al., N. Engl. J. Med., 1992). The adult human body contains slightly more than 1 kg of calcium, 99% being found in bone and teeth. Calcium is the principal cation of bone and exists in bone in an imperfect form of hydroxyapatite ($Ca_{10}(PO_4)_6(OH)_2$). Magnesium plays a key role in mineral metabolism (see Fatemi, S, J. et al., Clin. Endocrinol. Metab., 1991) and constitutes 0.5%-1% of bone ash. Magnesium influences the formation and/or secretion of hormones that regulate skeletal homeostasis and the effect of these hormones on bone. As a potassium salt, citrate decreases the urinary excretion of calcium thus keeping calcium in the bone, preserving bone mass (Koenig, K. et al., J. Urol., 1991). Potassium provides an alkali load (see Vescini F, J. et al., Endocrinol. Invest., 2005), counteracting diet-dependent acid production. Sodium fluoride has been used to decrease vertebral fracture risk (Pak Y. C. et al., J. Clin. Endocrinol. Metab. 1989; Lehmann R, et al., Bone, 1998) while strontium-containing compounds have long been suggested as an essential nutrient for the normal development, function and health of bone systems (see Meunier, P. J., N. Engl. J. Med., 2004). Strause found that bone loss in calcium-supplemented older women could be further arrested by concomitant increases in trace mineral intake using zinc, manganese and copper (see Strause, L., 1994).

Over the past few years, potassium magnesium citrate (U.S. Pat. Nos. 5,219,889; 5,432,200; 7,091,246) and potassium calcium citrate (U.S. Pat. No. 6,287,607) have been investigated as new types of dietary supplements in urinary tract and bone health respectively.

Coordination polymers have been described in the literature. Metal coordination complexes are compounds where a ligand bridges between metal centers, where each metal center binds to more than one ligand to create an "infinite" array of metal centers, e.g., a polymer (Wikipedia, "Coordination Polymers," 2008). Specific coordination polymers are defined in Oh, M. and Mirkin, C. A., Nature, 2005; and Luisi, B. S., et al., ChemComm. 2007).

SUMMARY

Applicants have prepared coordination compounds containing two nutritionally desirable cations and two nutritionally desirable anions. These coordination compounds, also referred to herein as "coordination complexes," are useful to provide these compounds in single-dosage form to provide for convenience in administration and increase patient compliance with recommended nutritional therapies. A structure of a potassium magnesium citrate fluoride $(K_3Mg_3Cit_2F_3)_n$ polymer illustrative of this new type of coordination polymer is depicted below:

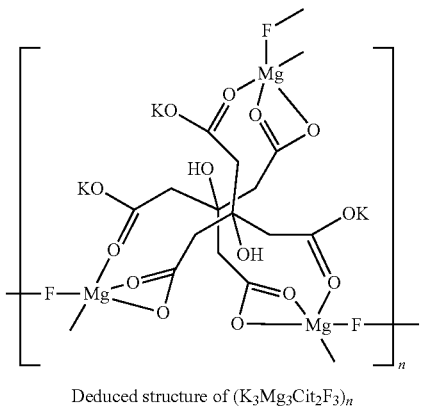

Deduced structure of $(K_3Mg_3Cit_2F_3)_n$

In the above structure, "n" indicates the polymeric structure of the compound. The compound can also include 0 to about 12 or more waters of hydration. The compounds of this invention can be in the form of crystals, powders, gels, suspensions and solutions. In the above structure, the citrate ions form the backbone of the polymer and the fluorine atoms are strongly associated with the calcium and magnesium atoms.

This disclosure also provides methods for making the subject compounds. In an embodiment, salts of the desired elements are mixed together in solution and the solvent removed to form a gel which is further dried to form crystals. Stirring must be continued until after the gel is formed to prevent sticking in the mixer. Drying can be done by spreading the gel on trays. For large-scale preparation of the compounds, spray drying, e.g., from a 50% (by weight) solution, is advantageous to produce the compounds in powder form. It is not necessary to preserve the crystalline form.

The compounds provided herein are fluoride compounds having two cations and two anions, such as for example, potassium magnesium citrate fluoride and related compounds. Also provided herein are pharmaceutical compositions containing such compounds. Further provided herein are methods of using the compounds and compositions as bone loss prevention agents, dietary supplement agents, agents for adding to water systems as a source of fluoride, and as agents for preventing dental caries, e.g., as fluoride treatments, and in toothpaste or liquid concentrates.

DETAILED DESCRIPTION

Figure 1:
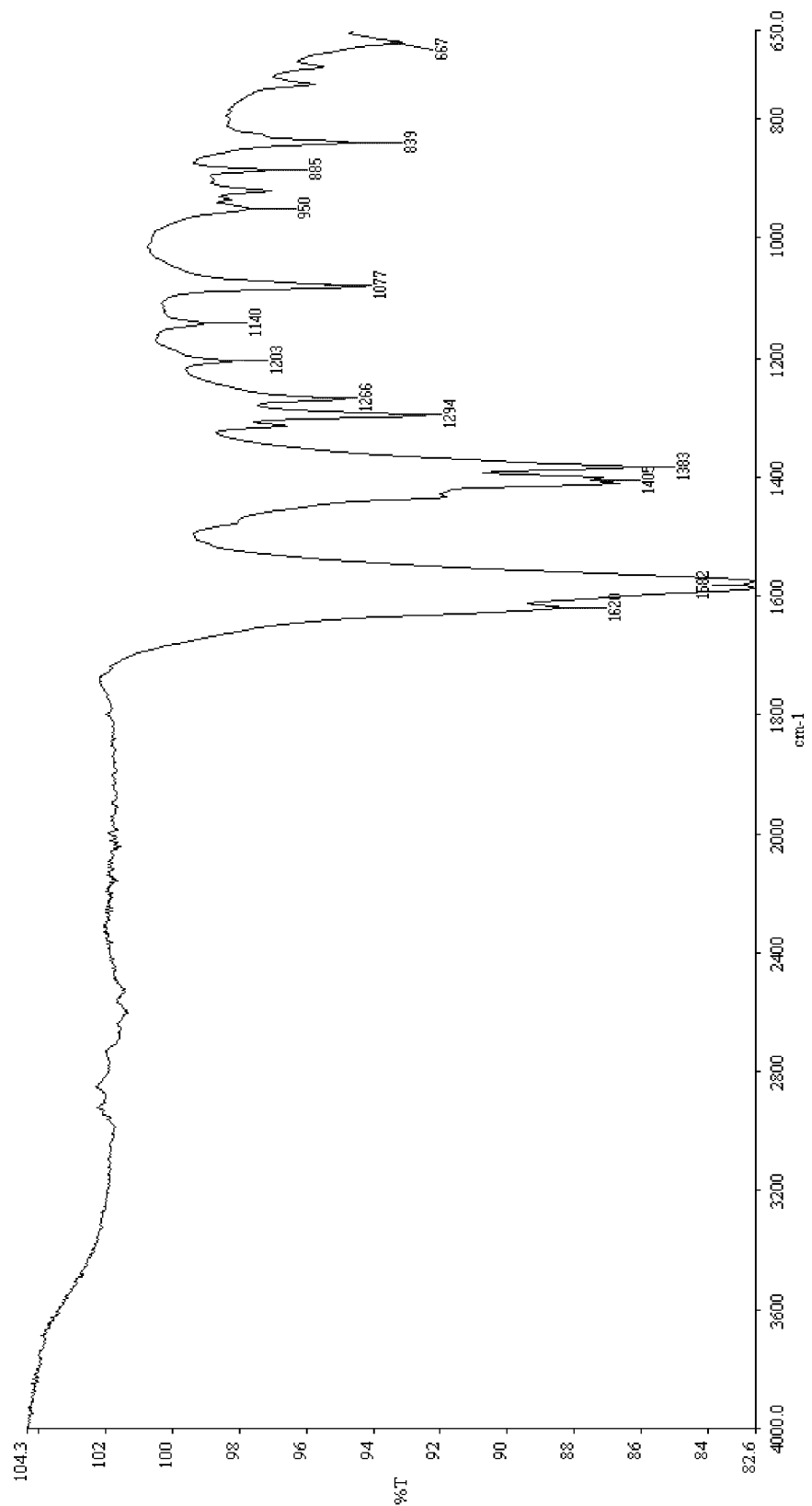
FIG. 1: FTIR spectrum of $K_3Mg_3Cit_2F_3$.
Figure 2:
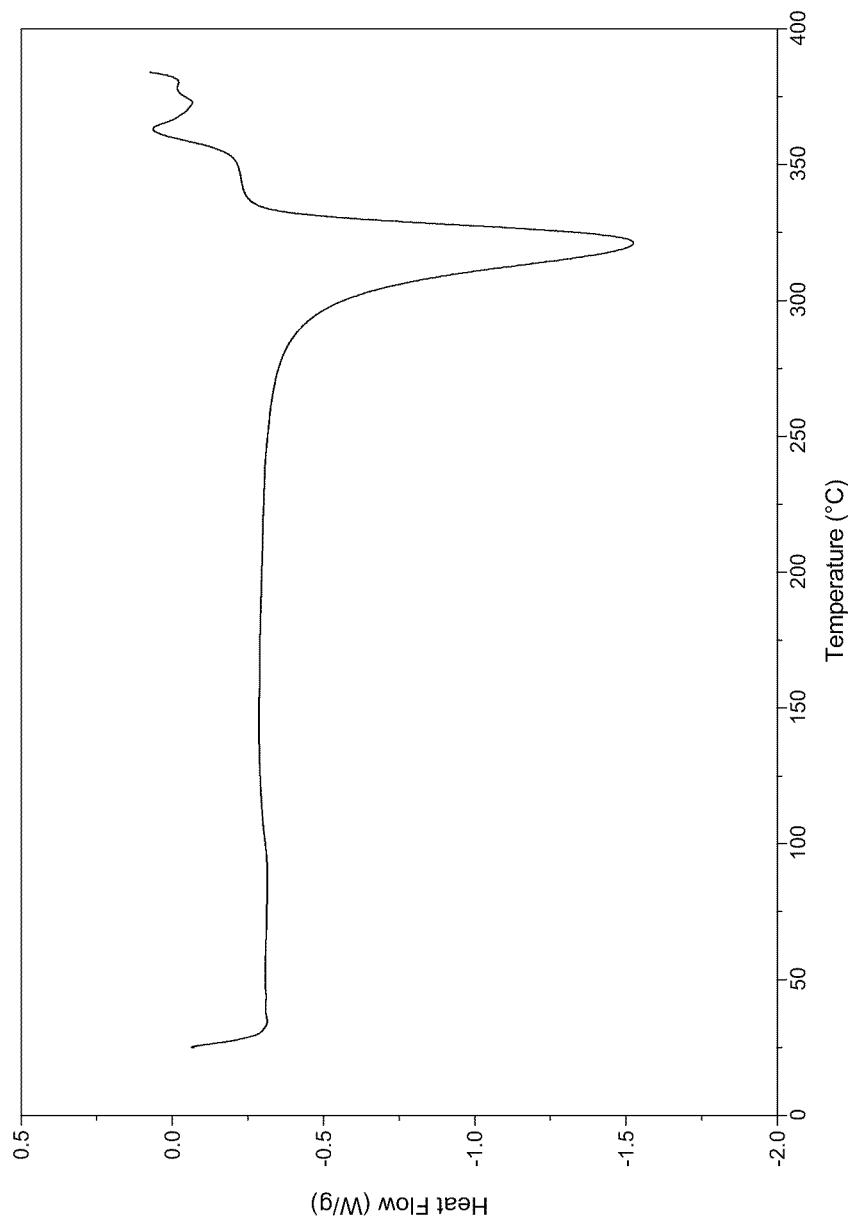
FIG. 2: DSC (differential scanning calorimetry) curve of $K_3Mg_3Cit_2F_3$.
Figure 3:
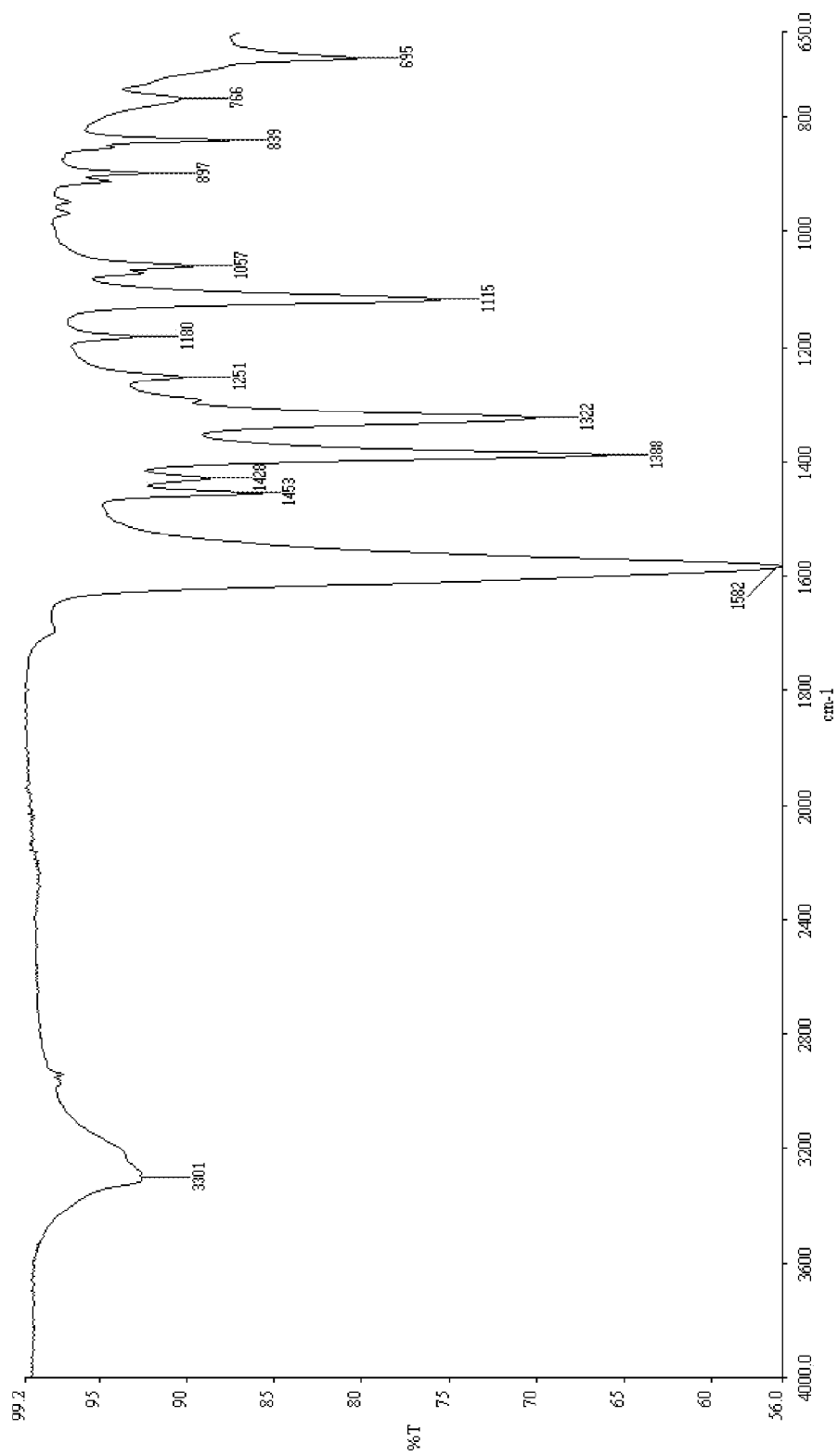
FIG. 3: FTIR (Fourier Transform Infrared) spectrum of $K_7MgCit_2F_3$.
Figure 4:
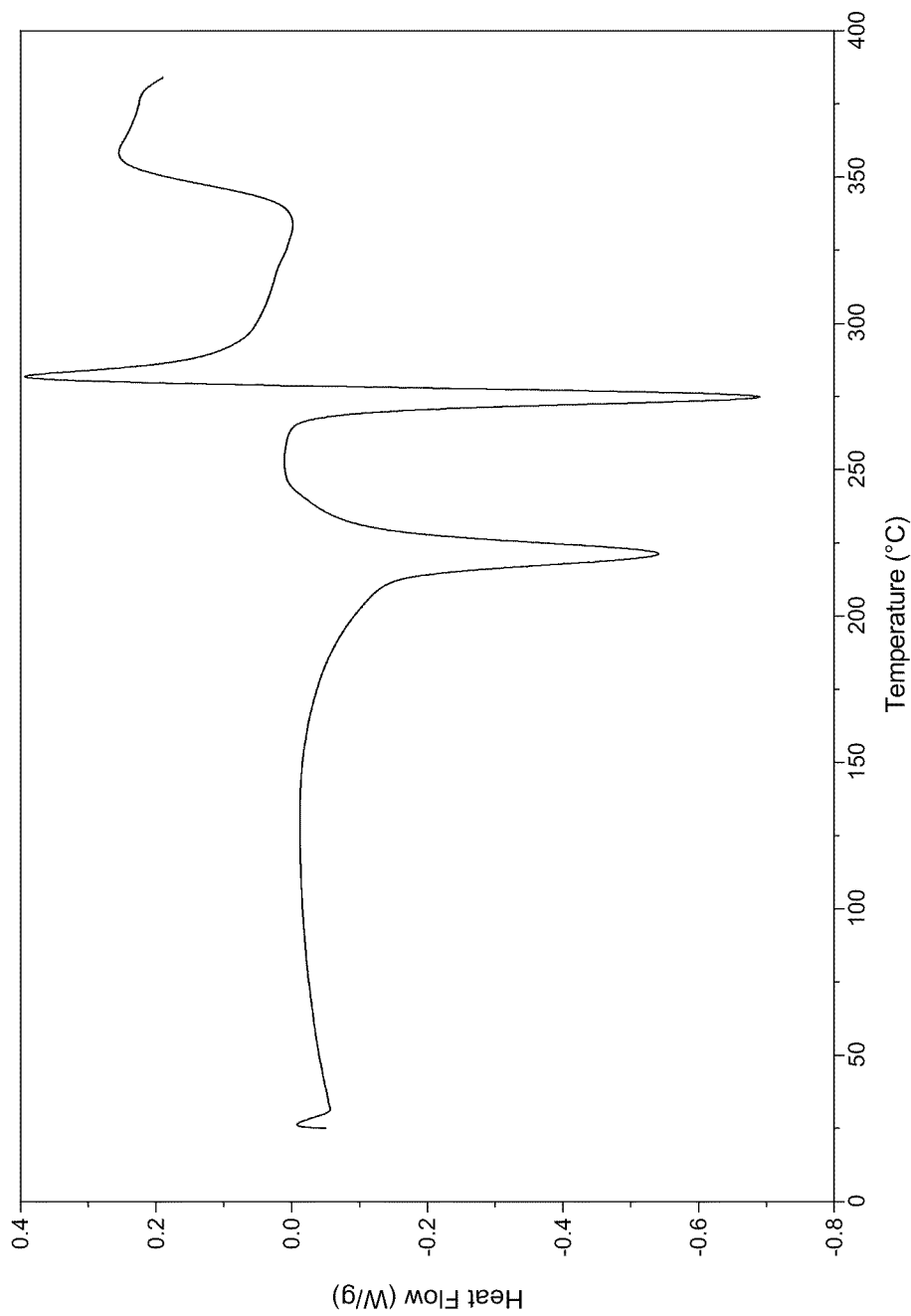
FIG. 4: DSC curve of $K_7MgCit_2F_3$.

With osteoporosis affecting 10 million people in the United States and with another 34 million having low bone mass, safe, effective therapies that have a high tolerability are needed. Since most adult bone mass is acquired during childhood and adolescence, it is important to begin building strong bones at an early age. One way to build strong bones is to provide the body's anabolic systems with the appropriate building blocks and the correct environment for building bone apatite. The compounds provided herein can be used in prevention and treatment of osteopenia and osteoporosis. Approved osteoporosis therapies reduce the risk of vertebral fractures, non-vertebral fractures and hip fractures, but compliance with current therapies is low. For example, patients are sometimes reluctant to take non-prescription calcium supplements which are not covered by their health insurance or Medicare plans. Also, some pharmaceuticals used for bone therapies have side-effects. For example, bis-phosphonates have been implicated in esophageal cancer and ulcers. Patients may also be reluctant to swallow multiple large tablets. Thus optimal anti-fracture efficacy may not be achieved in clinical practice. The present compounds are useful as preventives of osteopenia or osteoporosis by supplying two anions and two cations in a single convenient dosage form that supports healthy bone and maintains good compliance.

The family of compounds, useful as pharmaceuticals, provided herein comprises certain IA and IIA elements with citrate and fluoride in one molecule. In these compounds, citrate anions serve as bridging ligands.

Citrate acts through coordination covalency to bind the various cations and anions into a new entity and also provides a transient alkaline load to the body upon absorption, helping to maintain calcium in bone. Various cation components of these citric fluoride compounds, such as potassium, calcium, and magnesium, have been selected for their contribution to overall bone health. Certain transition metals can also be used in the citric fluoride compounds for bone health.

The classes of coordination complexes (also referred to herein as "compounds") described herein are constructed from "dual cation and dual anion" building blocks. The compounds are selected from the group of complexes in which the cations and anions satisfy the general formula: $A_xB_yCit_2F_z \cdot mH_2O$, wherein cation A is selected from certain IA or IIA metal ions in the Periodic Table, cation B is selected from certain IIA metal ions and divalent d-block transition metal ions, including but not limited to manganese (II), Zinc (II) and copper (II). "Cit" (citrate anion) is tribasic citric acid ($C_6H_8O_7^{-3}$) anion, and fluoride is the second anion. The stoichiometric values, x, y and z, are selected as described below, and m is determined by drying time.

In an embodiment, the coordination complex is synthesized directly from the reaction of suitable reactant solutions and the precipitate is collected by filtration. In an embodiment, the coordination complex is synthesized from a reaction of reactant solutions via polymer gel formation, and this is followed by dehydration and crystallization. In another embodiment, the coordination complex is synthesized from a gel solution via a spray drying process. Other equivalent means of preparing the complex can be determined by those skilled in the art without undue experimentation.

The coordination complexes form via both coordination and ionic bonding. The tribasic citric acid ions serve as bridging ligands between metal centers, where each of the metal centers binds to more than one ligand in the complex. The structural features and composition of the synthetic coordination complexes have been characterized by Fourier Transform Infrared (FTIR), Differential Scanning Calorimetry (DSC), Nuclear Magnetic Resonance (NMR), Inductively Coupled Plasma Optical Emission Spectrometer (ICP-OES), and Liquid Chromatography (LC) methods. Other means known to the art for characterizing the complexes described herein can also be used, including X-ray Diffraction (XRD).

An embodiment hereof is a potassium magnesium citric fluoride coordination complex. This heterometal heteroligand complex has two cations, potassium and magnesium, and two anions, fluoride and citrate, all ions having a positive impact on bone health. This unique composition has been developed to be taken as a dietary supplement providing potassium, magnesium, citrate and fluoride, administration of which counters bone loss associated with aging or menopause.

Each component of the potassium magnesium citric fluoride compound contributes to healthy bone. Magnesium is part of the bone hydroxyapatite lattice. Fifty to sixty percent of normal total body magnesium resides in bone. One-third of skeletal magnesium is surface-limited and exchangeable, while the remainder of magnesium in bone is in the hydroxyapatite lattice and is released during bone resorption. Fluoride ions substitute for hydroxyl ions in hydroxyapatite. There is general agreement that fluoride stimulates bone formation directly without the need of prior bone resorption. This can explain why fluoride is so effective in increasing bone mass. Potassium and citrate both provide a metabolic alkaline load. A transient alkaline load helps maintain calcium in bone, using less calcium from bone to neutralize the usual Western acidic diet. Delivering an alkaline load counters bone loss by partly compensating for the cumulative buffering effect that skeletal sources provide against diet-dependent acid production.

Delivering an alkaline load means that the composition is delivering, for absorption through the GI tract, mineral cations that are not degraded (though the anions may be metabolized). Potassium cations are more readily absorbed through the GI tract than, e.g., calcium or magnesium, and thus deliver a greater level of alkali load.

In other embodiments hereof, other IA and IIA metal ions can be used. The benefit of using calcium as one of the cations is that it is important in bone health and fluoride should be given with calcium as a building block for new bone. Chemically, potassium is interchangeable with sodium in this invention; however, potassium has more beneficial effects on bone due to its metabolic alkaline load. Strontium and manganese have also been found to be beneficial in bone health and can be used as Cation A or Cation B.

The citric fluoride complexes provided herein can be used as drug dietary supplements for bone health, additives in water to provide fluoridation and/or can be used in dental practice; e.g., in toothpaste or liquid concentrate for bone health.

The compounds (complexes) provided herein are represented by the formula:

$$A_xB_yCit_2F_z,$$

wherein:
A is a cation selected from the group consisting of the Periodic Table IA metal ions lithium (Li), sodium (Na), and potassium (K) and the Periodic Table IIA metal ions Magnesium (Mg), Calcium (Ca), Strontium (Sr), and Barium (Ba);
B is a cation selected from the Periodic Table IIA metal ions Magnesium (Mg), Calcium (Ca), Strontium (Sr), and Barium (Ba), and the Periodic Table divalent d-block transition metal ions Chromium (Cr), Manganese (Mn), Iron (Fe), Copper (Cu), and Zinc (Zn);
A and B are different;
"Cit" is tribasic citric acid anion;
the ratio of x to y is equal or higher than 1.0 but lower than 8.0;
z is selected such that electroneutrality is preserved; and
wherein z is adjusted so that when A and B are both selected from ions having a valence of plus 2, 2x+2y is equal to z+6; or
wherein z is adjusted so that when A is selected from ions having a valence of plus 1 and B is selected from ions having a valence of plus 2, x+2y is equal to z+6.

The general formula, $A_xB_yCit_2F_z$, as well as specific formulas encompassed by this general formula that do not specify the presence of bound waters include compounds having no bound waters, or any number of bound waters. In the general formula, $A_xB_yCit_2F_z.mH_2O$, and specific formulae encompassed by this general formula, m is 0-12. Separate classes of compounds provided herein can be formed from any combination of these elements.

One class of compounds is represented by a formula selected from the group consisting of: $A_3Mg_3(C_6H_5O_7)_2F_3$; $A_6Mg_3(C_6H_5O_7)_2F_6$; and $A_7Mg(C_6H_5O_7)_2F_3$; wherein A is potassium or sodium.

Another class of compounds is represented a formula selected from the group consisting of: $A_3Ca_3(C_6H_5O_7)_2F_3$; $A_6Ca_3(C_6H_5O_7)_2F_6$; and $A_7Ca(C_6H_5O_7)_2F_3$; wherein A is potassium or sodium.

Another class of compounds is represented by a formula selected from the group consisting of: $A_3Sr_3(C_6F_5O_7)_2F_3$; $A_6Sr_3(C_6H_5O_7)_2F_6$; and $A_7Sr(C_6H_5O_7)_2F_3$; wherein A is potassium or sodium.

Another class of compounds is represented by a formula selected from the group consisting of: $A_5Mg(C_6H_5O_7)_2F$; $A_5Ca(C_6H_5O_7)_2F$; and $A_5Sr(C_6H_5O_7)_2F$; wherein A is potassium or sodium.

Another class of compounds is represented by a formula selected from the group consisting of: $Mg_2Ca_2(C_6H_5O_7)_2F_2$; $Mg_2Sr_2(C_6H_5O_7)_2F_2$; and $Sr_2Ca_2(C_6H_5O_7)_2F_2$.

Another class of compounds is represented by the formula: $A_2B_2(C_6H_5O_7)_2F_2$, wherein A is selected from Magnesium, Calcium, Strontium, and Barium, and B is selected from Chromium, Manganese, Iron, Copper, and Zinc. In a particular embodiment, this compound is a compound wherein B is selected from the group consisting of zinc(II), manganese(II) and copper(II).

In another class, A is selected from the group consisting of Na and K.

In another class, the Periodic Table Group IIA ions are selected from the group consisting of Mg, Ca, and Sr. In another class, B is selected from Cr, Cu, Zn, and Mn.

In another class, in which A is potassium and B is magnesium, the ratio of potassium to magnesium is greater than 4:1.

It will be appreciated that numerous different compounds can be formed by one skilled in the art without undue experimentation, depending on the values of x, y, and z, and the ions encompassed within the definitions of A and B. Compounds having each possible value of x comprise a separate class of compounds. Compounds having each possible value of y comprise a separate class of compounds. Compounds having each possible value of z comprise a separate class of compounds. Compounds having each possible element of A comprise a separate class of compounds. Compounds having each possible element of B comprise a separate class of compounds. Additional classes of compounds include compounds in which A excludes one of the Group IA ions, in which A excludes one of the Group IIA ions, and classes in which B excludes one of the Group IIA ions, as well as classes in which B excludes one of the divalent d-block transition metal ions. The classes defined above can be overlapping.

The compounds provided herein, being single compounds, rather than mixtures of separate compounds, provide advantages over mixtures of compounds containing the same elements in allowing convenient compounding into dosage forms for administration of proper dosages. If the desired elements useful for bone therapy were administered as separate salts, a much larger oral dosage form would be required, which would be hard for patients to swallow. Not only can counter-ions for the desired elements that are used in typical pharmaceutical preparations of these elements be eliminated by the present compounds, but the crystalline forms of the present compounds place the elements in the most efficient configuration, such that they take up less space than otherwise. In addition, the ratios of these elements can be kept constant for better dosage control. Further, the solubility of separate ions in the complex is more homogenous, rather than different for each element being delivered as is the case when a separate salt of each desired element is administered. This allows more uniform delivery of these elements in therapeutic proportions. Thus, there is no need to formulate complicated dosage forms in which the more soluble ions, such as fluoride, are provided in time-release form while the less soluble elements are not.

A pharmaceutically acceptable composition is provided herein comprising one or more of the compounds described above in a pharmaceutically acceptable carrier. The pharmaceutically acceptable compositions can also contain carriers, fillers, binders, disintegrants, lubricants, slow-release agents, proteins, vitamins and coatings, all as known to the art.

Such pharmaceutically acceptable compositions include those in which the compound is present in an amount sufficient to exert anti-bone loss activity, is present in an amount sufficient to exert anti-osteoporosis or anti-osteopenia activity, is present in an amount sufficient to support new bone formation and prevent excessive resorption of calcium, is present in an amount sufficient to decrease fracture risk, and/ or is present in an amount sufficient to serve as a dietary supplement. Suitable dosages of the compounds for these purposes are known to the art and/or are readily determined by one skilled in the art based on art-known principles.

The pharmaceutically acceptable compositions can be in oral dosage forms selected from the group consisting of tablets, capsules, liquids, powders; or in buccal dosage forms such as films, quick-dissolve tablets, liquids, gel forms, pastes, suspensions, in topical preparations such as creams, in injectable and intravenous dosage forms.

The compounds provided herein can be prepared by a process comprising making an aqueous solution of compounds containing the component ions of the desired compound and obtaining the desired compound from the solution by a method selected from the group consisting of: crystallizing the desired compound from the aqueous solution; drying the desired compound from its gel solution or slurry; and drying an aqueous solution of the desired compound by a spray drying process, all as more fully described below.

Advantageously, the reactants are used in stoichiometric amounts corresponding to the compound being prepared. Advantageously, a "one-pot" method is used to make the complexes, wherein no washing or liquid-solid separations are required. This provides efficiency and avoids loss of material in the process. The cation donors are advantageously selected from carbonates, bicarbonates, oxides, hydroxides and citrates. Generation of toxic hydrogen fluoride gas is avoided. The water content of the reaction mixture is advantageously selected to be high enough to provide a matrix for one hundred percent incorporation of the cations into the complexes, but not so high as to require liquid/solid separation or unnecessary time and expense for drying. This water content is typically between about 25% and about 120% based on the weight of the solids. Advantageously, the reaction is conducted at a temperature high enough to promote the reaction, but not so high as to degrade the citrate and introduce byproducts such as oxides. Typically the temperature is between about 70 and about 90° C. and in embodiments, is about 80° C.

After the reaction product has formed, water is extracted from the product by drying, e.g., oven drying or spray drying. In an embodiment, the product is dried until an LOD assay of a sample of the product shows no more than 1% further water loss. Bound waters can be removed from the product at temperatures over about 100° C. At temperatures above about 120° C., citrate degrades, and therefore, drying at oven temperatures preferably takes place at temperatures between about 100 and 120° C. Typically, drying at these temperatures produces a complex having 4 bound waters of hydration. Removal of waters of hydration is desirable when reduction of molecular weight and volume of the complex is desired.

Methods of using the compounds to treat medical conditions are also provided herein. Such conditions can be selected from the group consisting of bone loss, osteoporosis, osteopenia, excessive resorption of calcium, dietary deficiency, and risk of fracture. The methods comprise administering to a patient in need thereof an effective amount of a pharmaceutically acceptable composition containing a compound provided herein. Further provided herein are methods for preventing bone loss and dental caries comprising administering to a patient in need thereof a pharmaceutically acceptable composition comprising a compound provided above.

Also provided herein are methods fluoridating a water system comprising adding to said water system a compound provided herein.

EXAMPLES

As illustrations, described herein are methods for producing potassium magnesium citric fluoride complexes. The compounds are synthesized by the reaction of magnesium citrate and potassium fluoride in aqueous solution in such proportions that the mixture thus formed comprises potassium ions, magnesium ions, citrate ions and fluoride ions and has the general formula $K_xMg_yCit_2F_z$.

In embodiments hereof, the crystalline $K_3Mg_3Cit_2F_3$ product is generated from the reaction solution. In other embodiments, a polymer gel is formed from the reaction solution and a dry powder product is obtained from the gel by vacuum-dried desiccation. In other embodiments, the drying step comprises spray drying. In other embodiments hereof, the cation other than potassium is calcium. $Ca_xMg_yCit_2F_z.mH_2O$ (z=2x+2y−6) is extremely useful in bone loss prevention. The other compounds falling within the scope of the claims hereof can be made by one skilled in the art without undue experimentation using methods analogous to those illustrated herein.

Example 1

Manufacture of Potassium Magnesium Citrate Fluoride

In one embodiment, the method of manufacture of potassium magnesium citrate fluoride comprised:

1. adding magnesium citrate and water to a mixing vessel to form a solution;

2. adding potassium fluoride and water to another vessel to form a solution;

3. mixing the solutions from steps (a) and (b) using a suitable means such as a mechanical mixer until a precipitate forms;

4. separating the formed precipitate from the solution using a suitable separation means such as filtration, centrifugation or other means known in the art; and 5. transferring the product to a vessel and drying the product using a suitable means known to the art.

The dried product can be compounded into a suitable dosage form, as shown in Table 1, which shows relative proportions of ionic components required to produce a dosage form of $K_3Mg_3(C_6H_5O_7)_2F_3$. For example, administration of fluoride as sodium fluoride in the amount of 11 mg. twice per day (bid) has been recommended to prevent lower vertebral fractures. As shown in the fourth data column of the "Components" section at the bottom of Table 1, this dosage could be supplied by administering $K_3Mg_3(C_6H_5O_7)_2F_3$ in a single tablet containing 11.3 mg F, 23.255 mg K, 14.456 mg Mg and 74.981 mg citrate twice a day, or by administering the same amount of these components in two tablets, each containing 5.65 mg F, 11.63 mg K, 7.23 mg Mg and 37.49 mg citrate, two times per day.

TABLE 1

| Calculated dose level of $K_3Mg_3(C_6H_5O_7)_2F_3$ in a tablet | | | | | |
|---|---|---|---|---|---|
| Citric Fluoride Compound | | Molecular Weight | | | |
| $K_3Mg_3F_3(C_6H_5O_7)_2$ | | 625.40 daltons | | | |
| if desire 4 mg of F per tablet | | | | | |
| F = | 18.9984 | | | | |
| 3F = | 56.9952 | | | | |
| Fractional amount | 0.09113 | | | | |
| How much of the candidate molecule do you need to provide 4 mg F? | | | 4 mg F | | |
| Amount of Candidate molecule needed is: | | 43.89141 mg | | | |
| How much Mg does this provide in this 4 mg F tablet? | | | How much Citrate does this provide in this 4 mg F tablet? | | |
| Mg = | 24.3050 | | Citrate = | 189.096 | |
| 3Mg = | 72.9150 | | 2Citrates = | 378.192 | |
| Fractional amount | 0.1165 | | Fractional amount | 0.6047 | |
| Amount of Mg in this tablet: | | 5.117272 mg | Amount of Citrate in this tablet: | 26.54202 mg | |
| | | | mEq of citrate in this tablet: | 0.421079 mEq | |
| How much K does this provide in this 4 mg F tablet? | | | | | |
| K = | 39.0983 | | | | |
| 3K = | 117.2949 | | | | |
| Fractional amount | 0.1875 | | | | |
| Amount of K in this tablet: | | 8.2319 mg | | | |
| Component | | mg/tablet | | | |
| F | 1.500 | 4.000 | 8.000 | 11.300 | 22.600 |
| K | 3.087 | 8.232 | 16.464 | 23.255 | 46.510 |
| Mg | 1.919 | 5.117 | 10.234 | 14.456 | 28.912 |
| Citrate | 9.953 | 26.542 | 53.084 | 74.981 | 149.962 |

Note:
74.981 mg Citrate/tablet is 1.18954 mEq

In an embodiment, a 1300 to 1500 mg tablet containing $K_3Mg_3(C_6H_5O_7)_2F_3$ tablet formulated for bone health can contain 500 IU vitamin $D_3$, 500 mg elemental calcium, 62-65 mg $K_3Mg_3(C_6H_5O_7)_2F_3$ (e.g. about 5.65 mg elemental F), as well as other typical components used in oral dosage forms such as a binder, e.g., 135 mg microcrystalline cellulose, a disintegrant, and a lubricant, such as 5-15 mg magnesium stearate. Other additives can include an agent to retard release of fluoride such as carnuba wax or hypromellose in order to prevent ulcer formation, used at about 10-15 percent of the tablet weight. An enteric coating can also be provided to prevent the tablet from dissolving in the stomach Example 2

Manufacture of Potassium Magnesium Citrate Fluoride

In another embodiment, the method of manufacture of potassium magnesium citrate fluoride comprised:
1. Adding magnesium citrate and water to a mixing vessel to form a slurry.
2. Adding potassium fluoride and water to another vessel to form a solution.
3. Adding slurry (a) to solution (b) and mixing using a suitable means such as a mechanical mixer.
4. Heating the mixture and removing water content until completion of the reaction (gel formation).
5. Cooling and transferring the product to a vessel and drying using a suitable drying system.

The compound can then be compounded into a dosage form using the active ingredient as prepared above, by the method illustrated in Table 1.

Example 3

Manufacture and Characterization of $K_3Mg_3Cit_2F_3$

In another embodiment, the method of manufacture of potassium magnesium citrate fluoride comprised:
1. 847.2 g (9 mol) of potassium fluoride dihydrate and 0.7 L of distilled (DI) water were added to a 2 L reaction vessel.
2. The mixture was mixed by a propeller mixer for 20 minutes at RT. A clear solution was obtained.
3. 1353.3 g (3 mol) of magnesium citrate anhydrous was added to the solution of Step #2 continuously for 1 hour.
4. The reaction vessel was covered and heated at 80° C. for 4 h.
5. The cover was removed from the vessel and 0.4 L of DI water was added.
6. The mixture was agitated until homogeneous.

7. The mixture was then cooled to room temperature (RT).
8. The product was transferred to a tray and dried in an oven at 135° F. overnight.
9. The dried mixture was milled to a white powder.

The compound can then be compounded into a dosage form using the active ingredient as prepared above, by the method illustrated in Table 1.

Characterization of the Product $K_3Mg_3Cit_2F_3 \cdot 4H_2O$.
Description: white microcrystalline product; melting point: 340° C.; FTIR: 1580, 1408, 1380, 1294, 1269, 1077, 837 and 667 cm$^{-1}$; DSC: single heat flow endotherm peak at 340° C.

Assay results are shown in Table 2:

TABLE 2

Analytic Assays for $K^+$, $Mg^{2+}$, by ICP-OES assay

| Items | $K^+$ | $Mg^{2+}$ |
|---|---|---|
| Assay | ICP-OES | ICPOES |
| Theoretical value (%) for $K_3Mg_3Cit_2F_3 \cdot 4H_2O$ | 16.82 | 10.45 |
| Experimental Result (%) | 16.69 ± 0.1 | 10.26 ± 0.1 |

The water content was confirmed by loss on drying (LOD) result.

TABLE 3

LOD of potassium magnesium citrate fluoride at 120° C. for 4 h

| Items | Sample 1 |
|---|---|
| Weight of pan/mg | 1140.3 |
| Weight of pan plus sample/mg | 1213.5 |
| Weight of sample | 73.2 |
| Weight Total of 2 h/mg | 1205.1 |
| Loss of water (%) | 11.5 |
| Weight Total of 4 h/mg | 1205.1 |
| Loss of water (%) | 11.5 |

TABLE 4

Water content calculated for $K_3Mg_3Cit_2F_3 \cdot 4H_2O$

| Item | FW |
|---|---|
| FW of $K_3Mg_3(C_6H_5O_7)_2F_3$ | 623.85 |
| FW of $K_3Mg_3(C_6H_5O_7)_2F_3 \cdot 4H_2O$ | 695.89 |
| Water % | 10.35 |

TABLE 5

Analytic Assays for $F^-$ and $(C_6H_5O_7)^{3-}$

| Items | $F^-$ | $(C_6H_5O_7)^{3-}$ |
|---|---|---|
| Assay | ISE | UPLC |
| Theoretical value (%) for $K_3Mg_3Cit_2F_3$ | 9.11 | 60.60 |
| Experimental Result (%) | 9.08 | 60.69 ± 0.03 |

Example 4

Synthesis of $K_7MgCit_2F_3$ $K_7MgCit_2F_3$ was prepared according to the following reaction scheme:

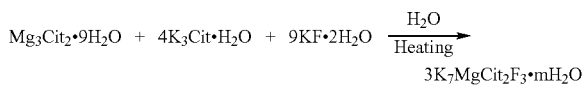

The compound was prepared as follows:
1. Potassium citrate monohydrate, 129.6 g (0.4 mol), magnesium citrate nonahydrate, 61.33 g (0.1 mol) and 150 mL of DI water were added to a 2000 mL beaker.
2. The beaker was covered with aluminum foil and then heated to 80° C. with a magnetic stirrer at low RPM for 1 h to afford a slurry.
3. Potassium fluoride dihydrate, 84.171 g (0.9 mol) was dissolved in 50 mL of DI water in a 100 mL beaker at RT and then this was added to the slurry in Step #2.
4. The resulting mixture was stirred at low rpm for 20 min to afford a clear gel solution.
5. The gel solution was then cooled to RT and dried in the air at RT to afford a white-colored crystalline product.

Characterization of the Product $K_7MgCit_2F_3$.
Description: white microcrystalline product; melting point: 225° C.; FTIR: 1582, 1453, 1388, 1322, 1251, 1180, 1115, 1057, 897, 839, 766 and 667 cm$^{-1}$; DSC: The first endothermic peak at 225° C. represents its melting point. The second endothermic peak at 275° C. is coupled by an exothermic peak due to decomposition.

Example 5

Preparation of $K_3Mg_3Cit_2F_3$ $K_3Mg_3Cit_2F_3$ was prepared using the following materials: $Mg_3Cit_2 \cdot 9H_2O$, 3.0664 g (5 mmol); $KF \cdot 2H_2O$, 1.41195 g (15 mmol); DI water 50 mL. The process steps were as follows:
1. The reactants were mixed in a 100 mL beaker and then DI water was added.
2. The reactants were heated to 80° C. maintained for 2 h.
3. The reactants were heated to evaporate water until gel formation and then the gel was cooled to RT.
4. The product was vacuum dried over $P_2O_5$ overnight to get transparent glass crystals.

Figure 5:
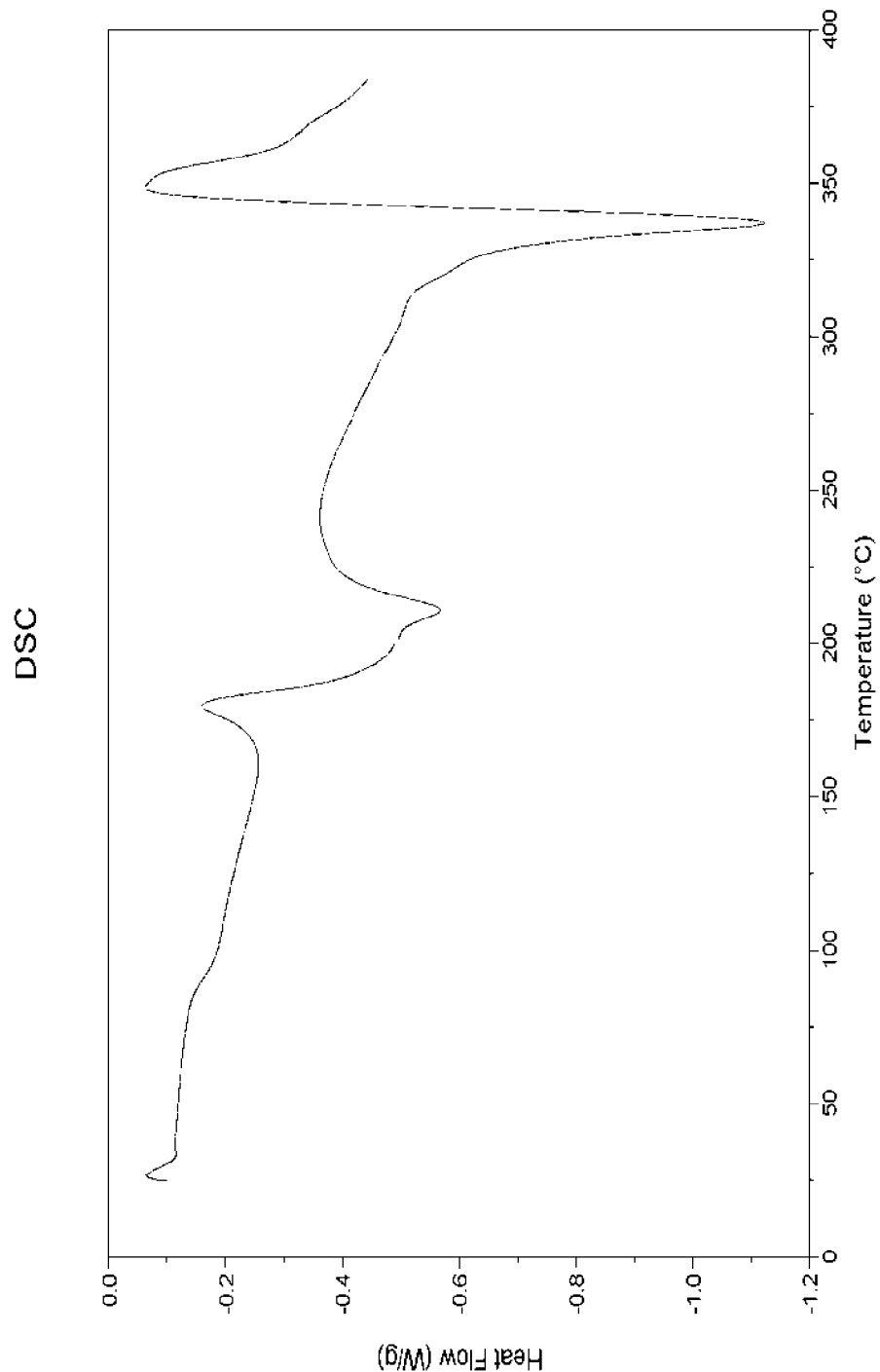
FIG. 5: DSC curve of $K_3Mg_3Cit_2F_3$ product prepared by the method of Example 5.
Figure 6:
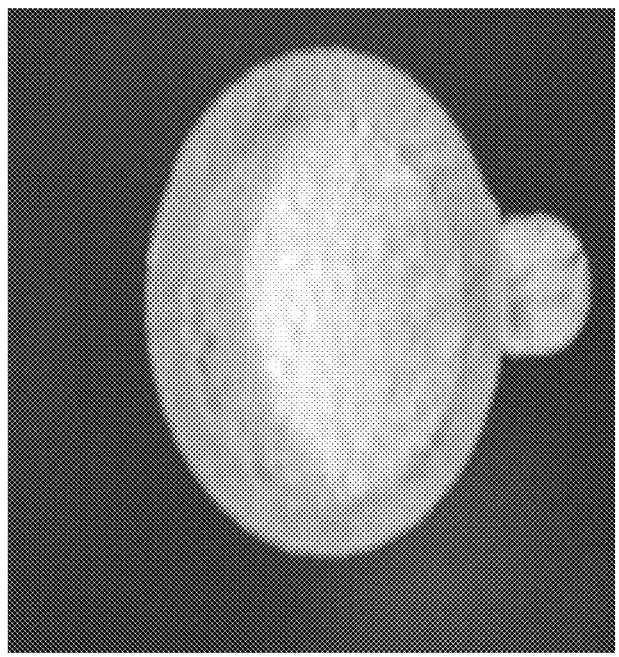
FIG. 6: Appearance of $K_3Mg_3Cit_2F_3$ product prepared by the method of Example 5.

A DSC curve for the product is shown in FIG. 5. The appearance of the product is shown in FIG. 6.

Example 6

Preparation of $K_3Mg_3Cit_2F_3$ $K_3Mg_3Cit_2F_3$ was prepared using the following materials: $Mg_3Cit_2$ anhydrous, 225.55 g (0.5 mol); $KF \cdot 2H_2O$, 141.2 g (1.5 mol); DI water, 18 mL (50% of starting material mass). The process steps were as follows:
1. The reactants were mixed with DI water in a 2000 mL beaker.
2. The reactants were then heated to 80° C. and the temperature maintained for 2 h with aluminum foil covering the beaker.
3. The beaker was uncovered, and stirring was maintained with heating for 2 h to remove water.
4. Upon gel formation, further heat was added and the reactants were mixed until dryness for 1 hour. Bottom material stuck on the beaker.
5. The product was removed (fairly difficult) to a dish and then dried in the air for 24 h. White-colored microcrystals were obtained.

Figure 7:
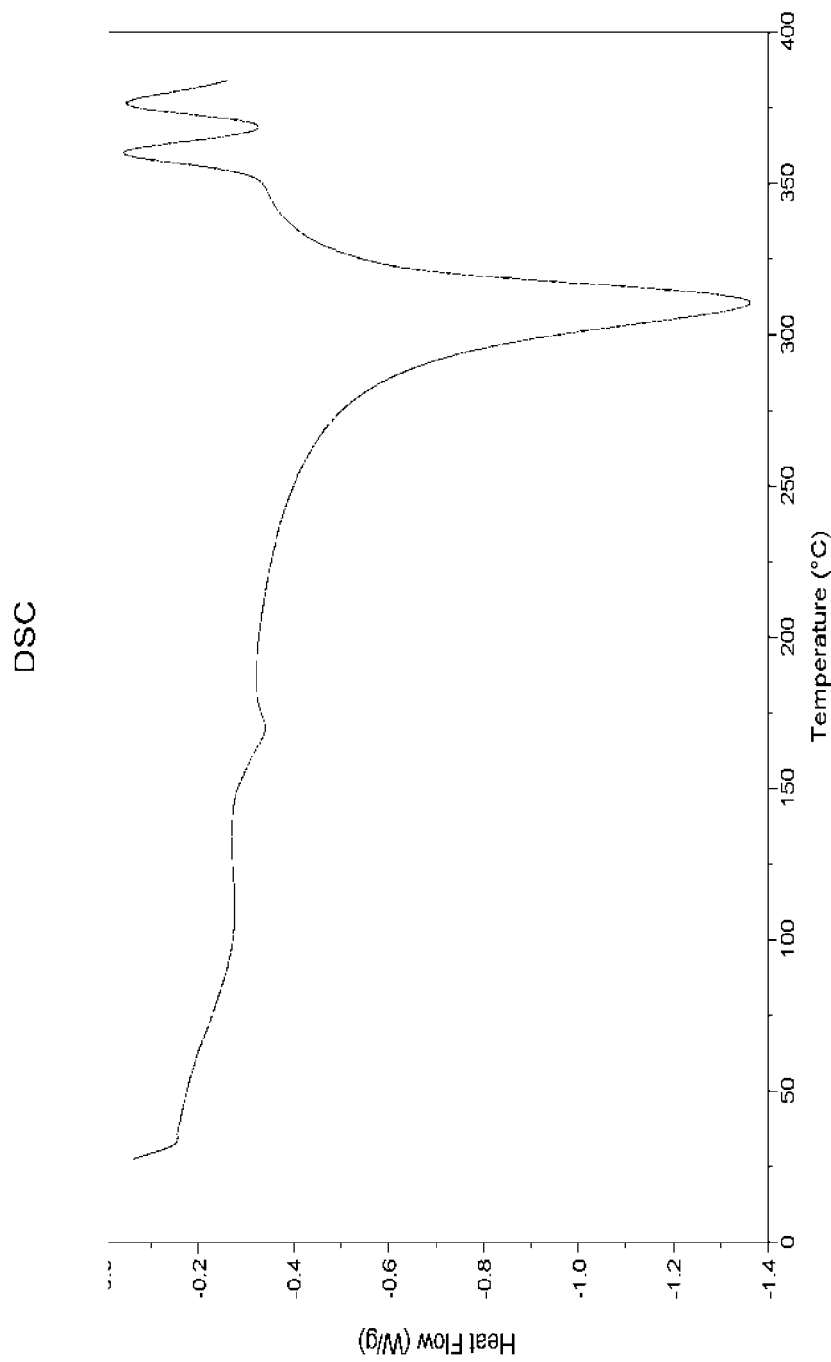
FIG. 7: DSC curve of $K_3Mg_3Cit_2F_3$ product prepared by the method of Example 6.
Figure 8:
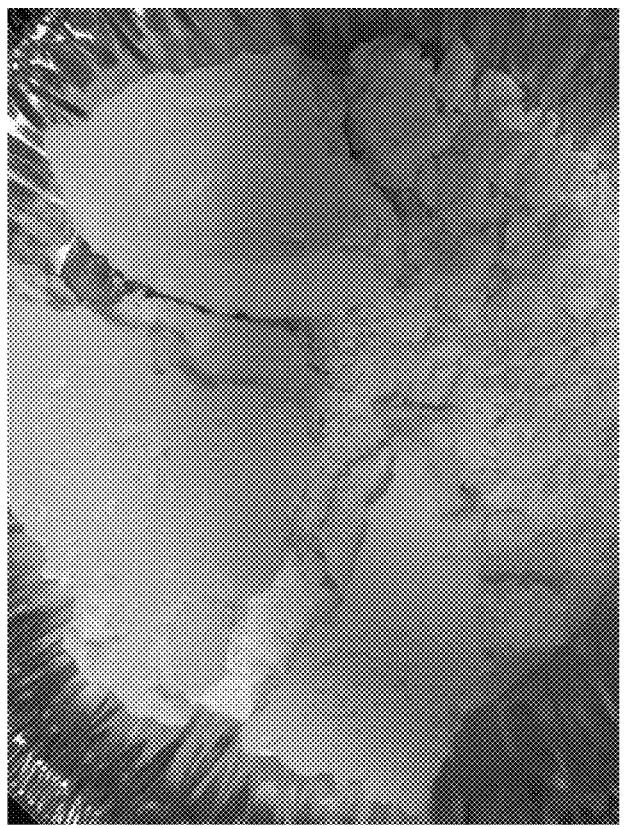
FIG. 8: Appearance of $K_3Mg_3Cit_2F_3$ product prepared by the method of Example 6.

A DSC curve for the product is shown in FIG. 7. The appearance of the product is shown in FIG. 8.

Example 7

Preparation of $K_3Mg_3Cit_2F_3$ $K_3Mg_3Cit_2F_3$ was prepared using the following materials: $Mg_3Cit_2.9H_2O$, 613.28 g (1 mol); $KF.2H_2O$, 282.39 g (3.0 mol); DI water, 224 mL (25% of starting material mass). The process steps were as follows:
1. The reactants were mixed with the distilled water in a 2000 mL metal container.
2. The reactants were heated to 80° C. and the temperature maintained for 2 h with aluminum foil covering the container.
3. The container was uncovered and stirring was maintained with heating for 1 h to remove water.
4. Upon gel formation, the product was further dried by until less dryness than in Example 6.
5. The product was transferred to a tray (difficult) and dried in the air. A white-colored microcrystalline product was obtained.

Figure 9:
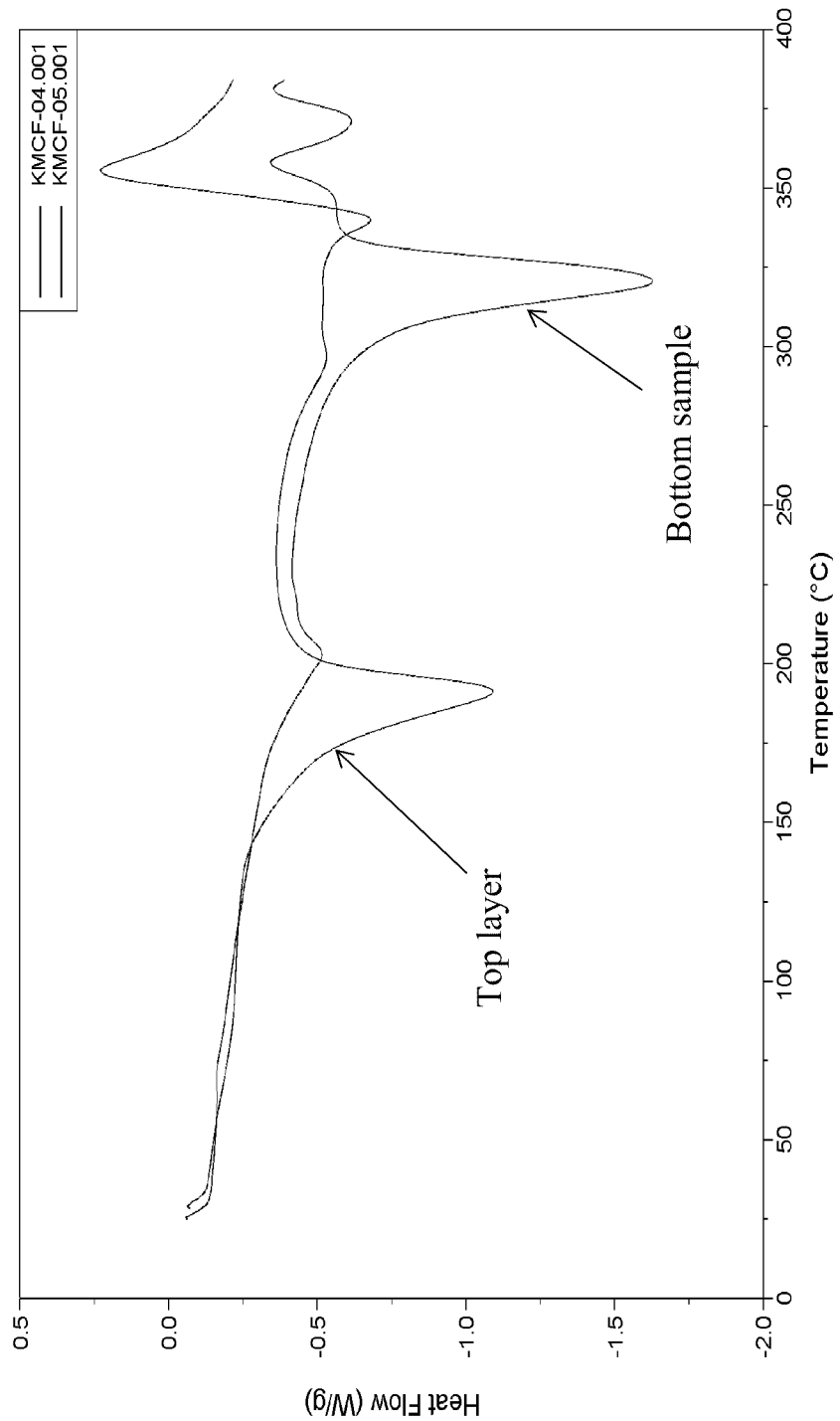
FIG. 9: DSC curve of $K_3Mg_3Cit_2F_3$ product prepared by the method of Example 7.
Figure 10:
FIG. 10: Appearance of $K_3Mg_3Cit_2F_3$ product prepared by the method of Example 7.

A DSC curve for the product is shown in FIG. 9. The appearance of the product is shown in FIG. 10.

Example 8

Preparation of $K_3Mg_3Cit_2F_3$ $K_3Mg_3Cit_2F_3$ was prepared using the following materials: $Mg_3Cit_2.9H_2O$, 306.64 g (0.5 mol); $KF.2H_2O$, 141.195 g (1.5 mol); and DI water, 450 mL (100% of starting material mass). The process steps were as follows:
1. The reactants were mixed with water in a 2000 mL beaker.
2. The beaker was covered with aluminum foil and heated to 80° C. with stirring at low RPM for 2 h.
3. The beaker was uncovered and stirring continued with heating for 1 h to remove water.
4. Upon gel formation, stirring was stopped and the temperature was maintained at 80° C. for 2 h.
5. The product was left at RT overnight, then transferred to aluminum foil and dried in the air. A white-colored microcrystalline product was obtained.

Figure 11:
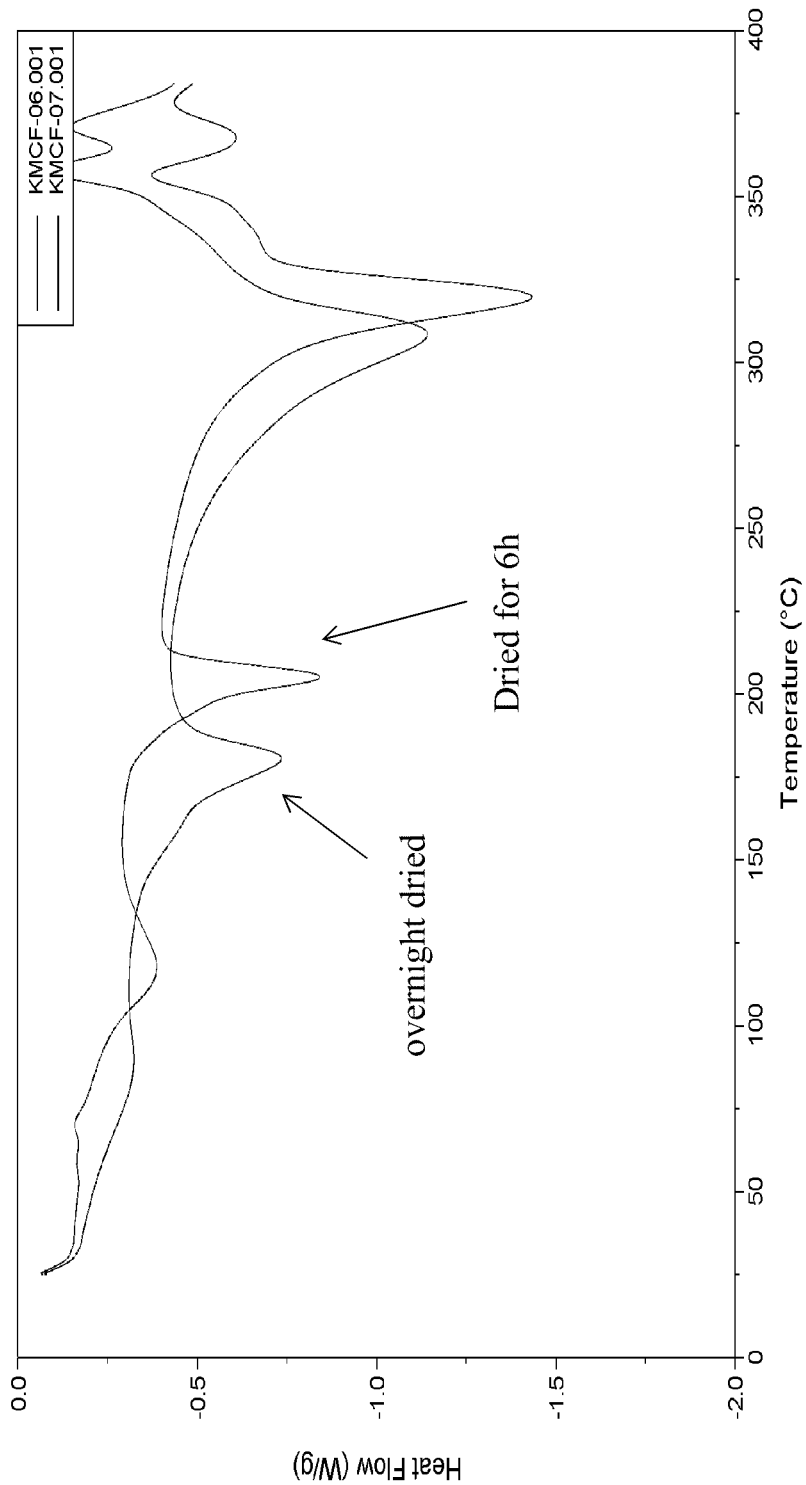
FIG. 11: DSC curve of $K_3Mg_3Cit_2F_3$ product prepared by the method of Example 8.
Figure 12:
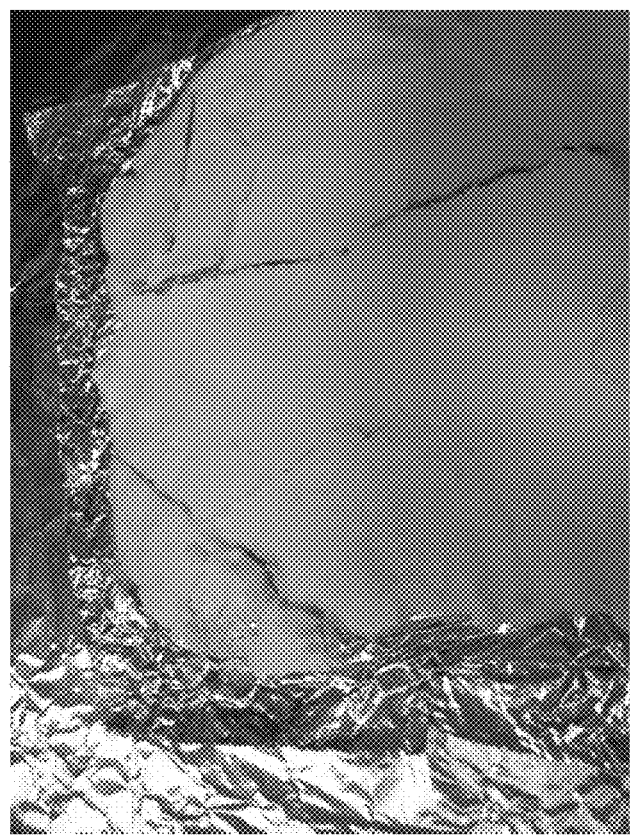
FIG. 12: Appearance of $K_3Mg_3Cit_2F_3$ product prepared by the method of Example 8.

A DSC curve for the product is shown in FIG. 11. The appearance of the product is shown in FIG. 12.

Example 9

Preparation of $K_7MgCit_2F_3$ $K_7MgCit_2F_3$ was prepared using the following materials: $Mg_3Cit_2.9H_2O$, 61.33 g (0.1 mol); $K_3Cit.H_2O$, 129.6 g (0.4 mol); $KF.2H_2O$, 84.717 g (0.9 mol); DI water, 200 mL. The process steps were as follows:
1. The potassium citrate, magnesium citrate and 150 mL water were mixed in a 200 mL beaker.
2. The beaker was covered with aluminum foil and heated to 80° C. with stirring at low RPM for 1 h to afford a slurry.
3. The potassium fluoride was dissolved in 50 mL of water and then this was added to the slurry.
4. The beaker agitated at low rpm for 20 min to get a clear gel solution.
5. The gel solution could be dried via a spray-drying process. However, it was air-dried in the beaker at RT to afford a white crystalline product. A white-colored microcrystalline product was obtained.

Figure 13:
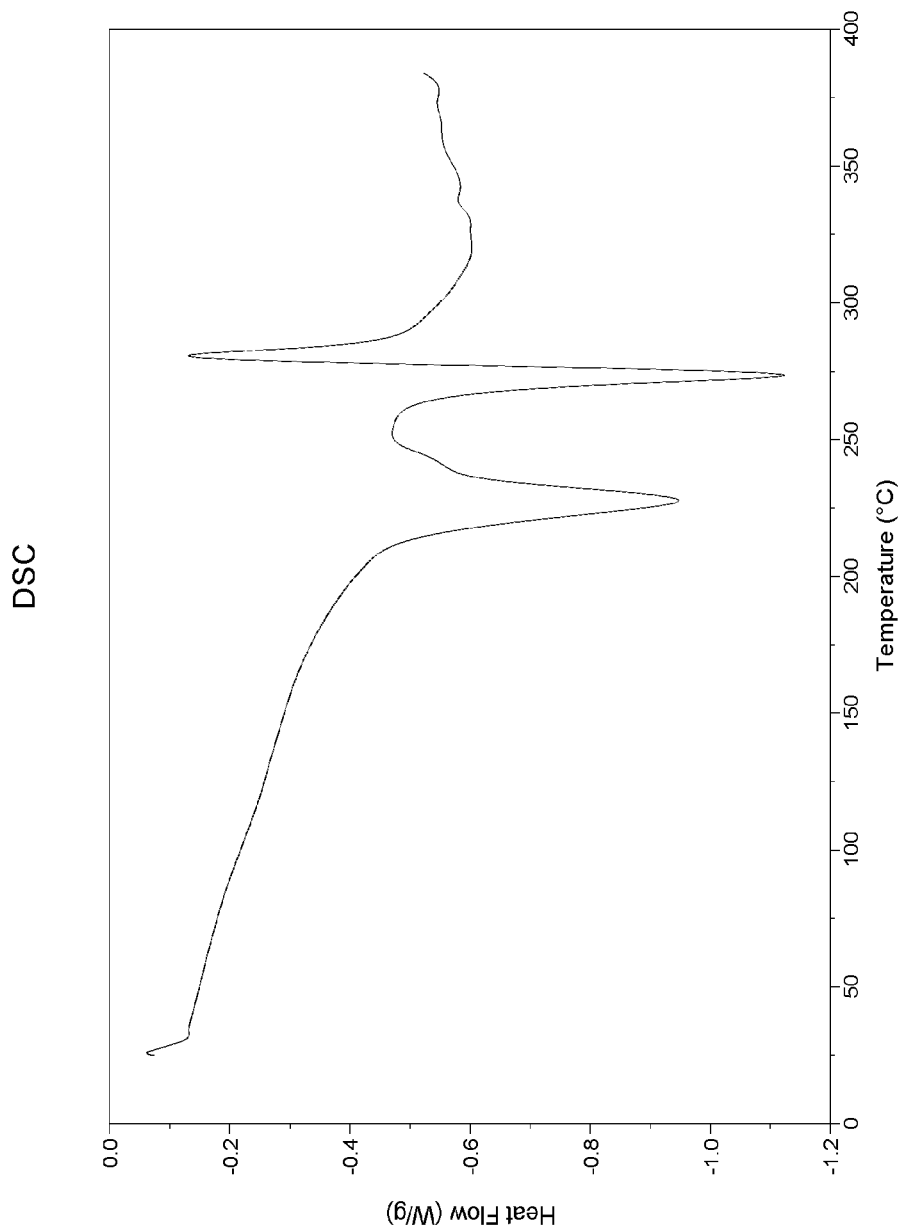
FIG. 13: DSC curve of $K_7MgCit_2F_3$ product prepared by the method of Example 9.
Figure 15:
FIG. 15: Appearance of $K_7MgCit_2F_3$ product prepared by the method of Example 9 using oven drying.
Figure 14:
FIG. 14: Appearance of $K_7MgCit_2F_3$ product prepared by the method of Example 9 using air drying.

A DSC curve for the product is shown in FIG. 13. The appearance of the transparent gel solution obtained in step 4 is shown in FIG. 14. The white crystalline product is shown in FIG. 15.

Example 10

Preparation of $K_3Mg_3Cit_2F_3$ $K_3Mg_3Cit_2F_3$ was prepared using the following materials: $Mg_3Cit_2$ anhydrous, 1353 g (3.0 mol); $KF.2H_2O$, 847.17 g (9.0 mol); DI water, 800 mL (36% of starting material mass). The process steps were as follows:
1. Potassium fluoride and 700 mL of water were added to a 2 L reaction vessel.
2. The mixture was heated to 80° C. to dissolve the crystals.
3. Magnesium citrate was added to the mixture of step 2 in powder form continuously over 1 h.
4. The mixture was agitated to complete the reaction and a gel product was formed. To this was added 100 mL of water.
5. The mixture was agitated further to eliminate any unreacted reactants and then cooled to RT.
6. The gel product was transferred to two trays. One of the trays was dried in the air at RT and the other one was dried in the oven at 60° C. for 24 h. A white microcrystalline product was obtained in both cases.

Figure 16:
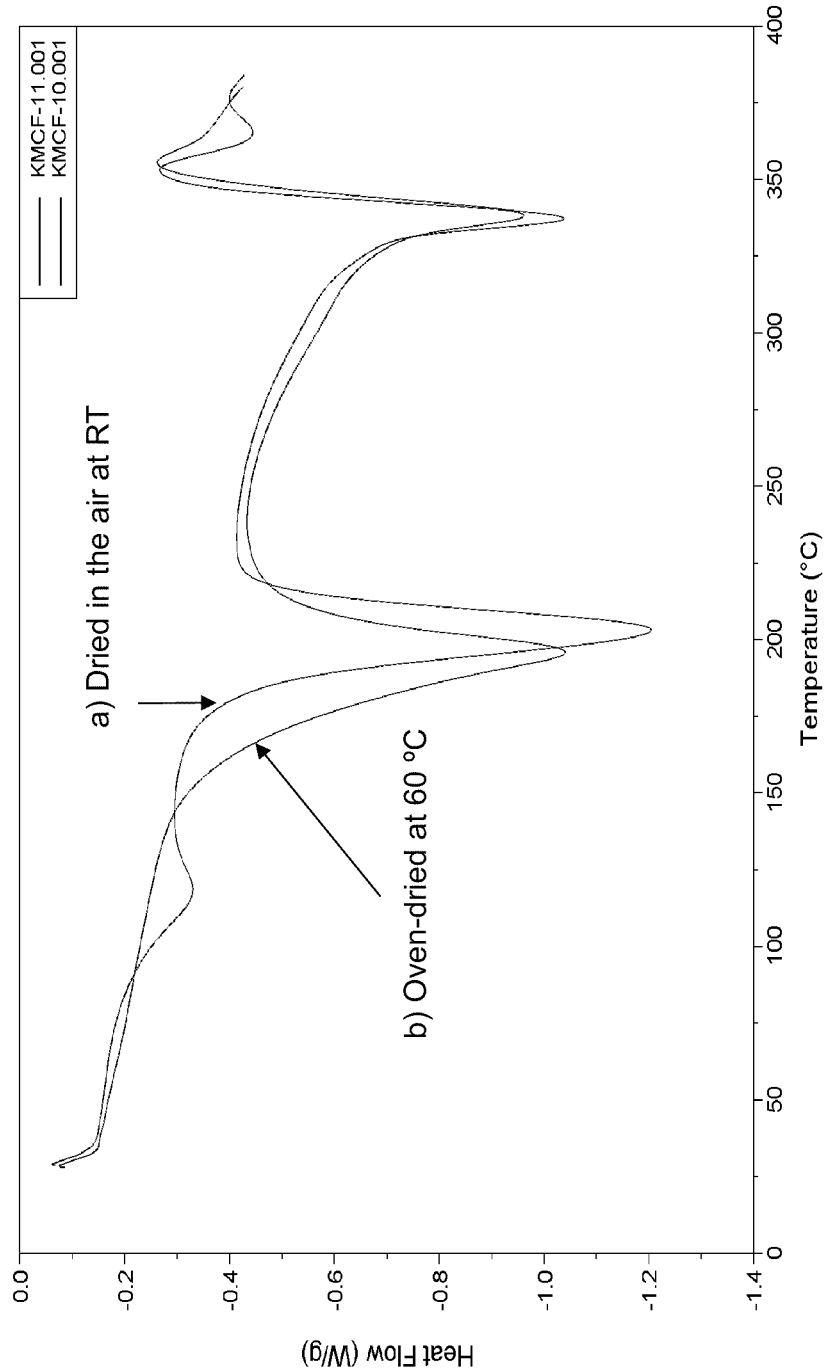
FIG. 16: DSC curves of $K_3Mg_3Cit_2F_3$ products prepared by the method of Example 10, and (a) dried in air at room temperature; and (b) oven-dried at 60° C. for 24 hours.
Figure 17:
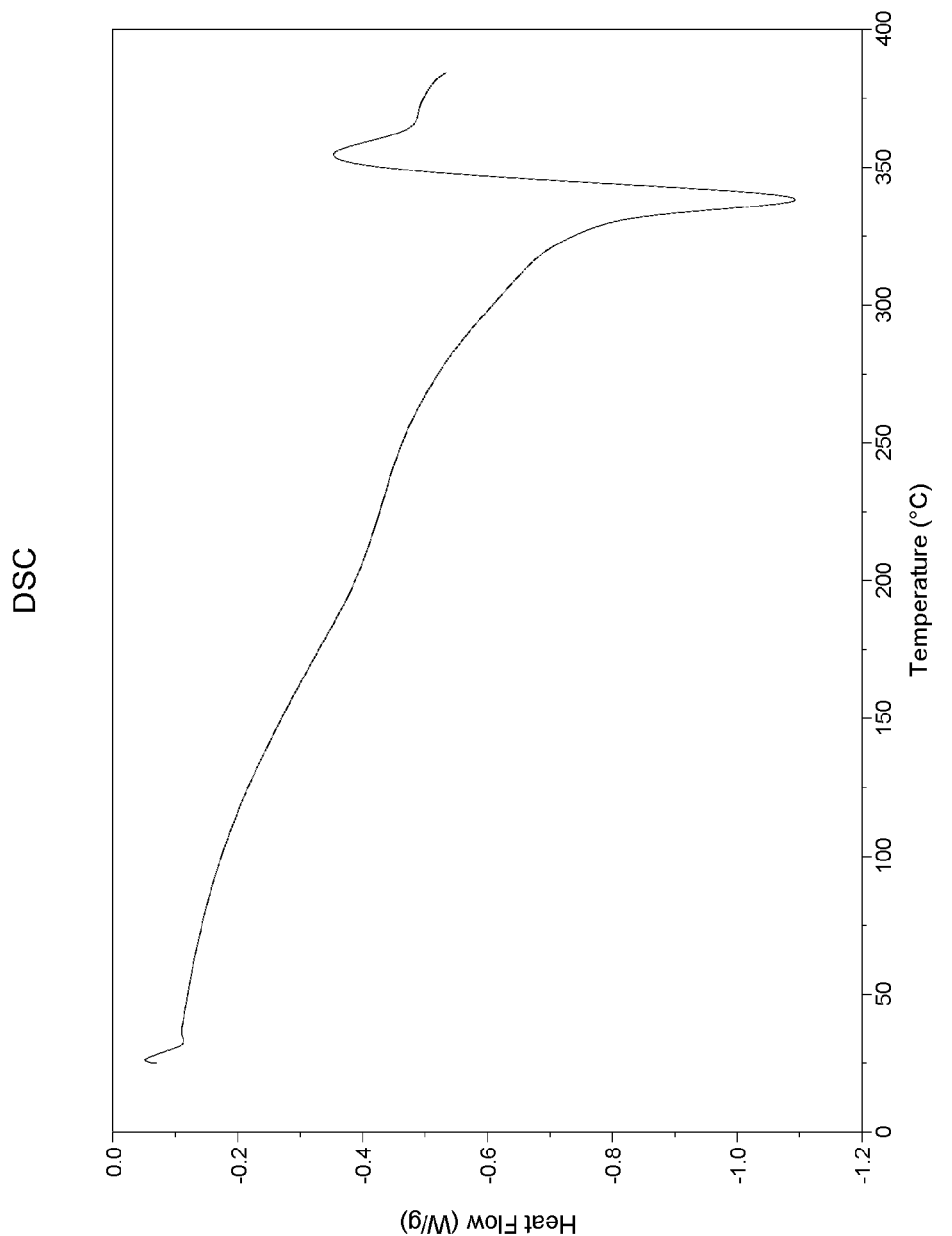
FIG. 17: DSC curve of $K_3Mg_3Cit_2F_3$ product prepared by the method of Example 10 after LOD (loss on drying), oven-dried at 120° C. for 4 hours.
Figure 18:
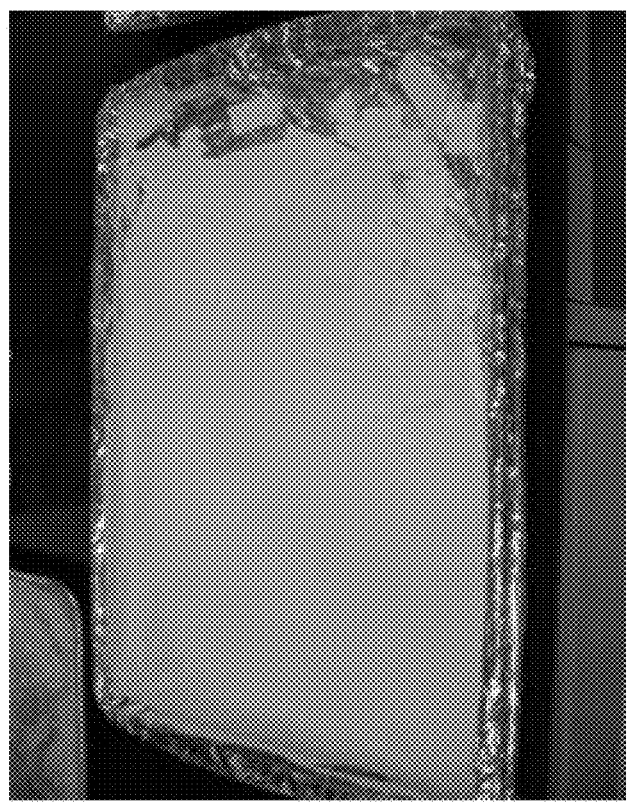
FIG. 18: Appearance of $K_3Mg_3Cit_2F_3$ product prepared by the method of Example 10 using air drying.
Figure 19:
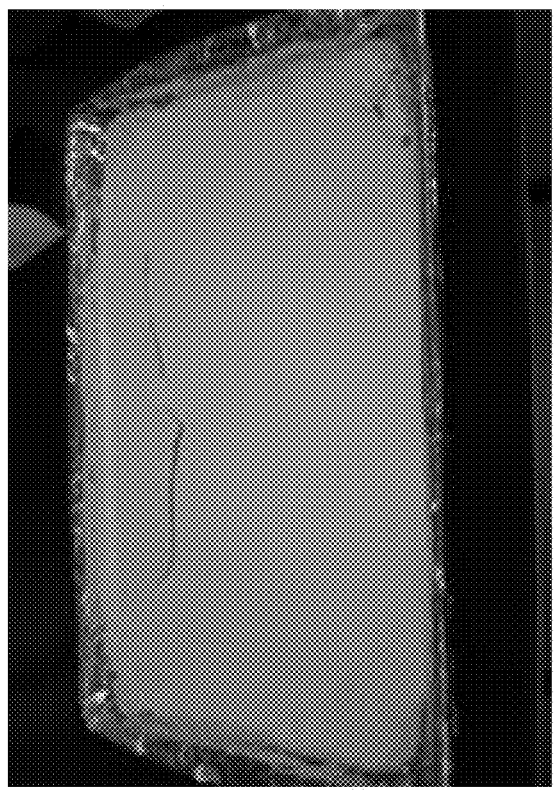
FIG. 19: Appearance of $K_3Mg_3Cit_2F_3$ product prepared by the method of Example 10 using oven drying.

DSC curves for the air-dried and oven-dried products are shown in FIG. 16. A DSC curve of the product after LOD (120° C. for 4 h) is shown in FIG. 17, indicating four waters of hydration are present in the complex. Comparison of the DSC results indicates that the DSC peak at around 200° C. is caused by dissociation of crystallized water molecules and the synthetic compound is highly thermal-stable up to 300° C. The appearance of the air-dried product is shown in FIG. 18. The appearance of the oven-dried product is shown in FIG. 19.

Example 11

Batch Manufacture of 20 Kg of $K_3Mg_3Cit_2F_3$

A 20 kg batch of $K_3Mg_3Cit_2F_3$ was manufactured by the following procedure:
1. Potassium fluoride dihydrate, 8.472 kg (90 mol) and 10.0 L of DI water were added to a 20 gallon LEE counter motion mixer (Lee industries, Inc. Model 2009MT).
2. The mixture was mixed at low RPM (40-50 rpm recommended) for 30 minutes at 60° C. to afford a clear solution.
3. Magnesium citrate anhydrous, 13.533 kg (30 mol) was added to Step #2 continuously over 1 hour.
4. The reaction vessel was closed and the temperature increased to 80° C. by circuit heating. After 1 h, the reaction solution became thicker (gel formation).
5. The mixer was switched off and lifted; attached material was scrubbed from the blade and large floating lumps on the surface of the solution were chopped.
6. The mixer was Immersed in the solution and agitation at the same speed resumed and maintained for an additional 3 h.
7. The lid of the reaction vessel was opened and 3.0 L of DI water was added.

8. The mixture was agitated until the system was homogeneous.
9. The temperature was then decreased to 50-60° C. by cooling.
10. After checking to make sure that the product temperature was in the range of 50-60° C. the product was transferred to trays from the bottom outlet of the reaction vessel.
12. The trays were put in the oven set at 190° F.
13. After drying overnight, the paste in the trays was broken up and the product put back in the oven for further heating.
14. A 1.0 g sample was taken from each tray and checked to make sure that its LOD was less than 1%.
15. To perform the LOD test, the 1.0 g sample of dried product was milled, optimizing the milling conditions to make sure the particle size was in the range of 125-150 μm. The finished product was a white powder.
16. 300 mg of the powder was transferred into a 43 mm aluminum pan. The pan and the sample were dried in an oven at 120° C. for 4 h. The LOD was found to be less than 1%.

Example 12

Formation of Macrocrystalline $K_7MgCit_2F_3$

Figure 20:
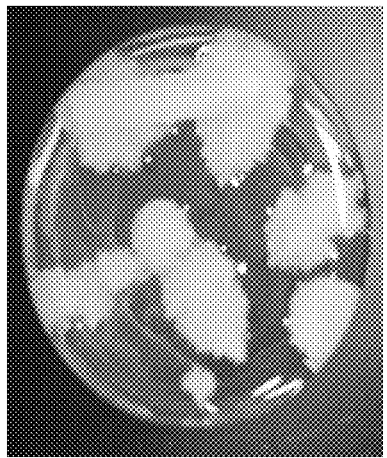
FIG. 20: Appearance of $K_7MgCit_2F_3$ macrocrystalline product described in Example 12.
Figure 20:
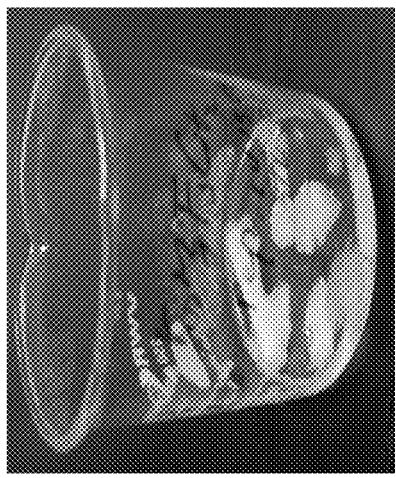
Figure 20:
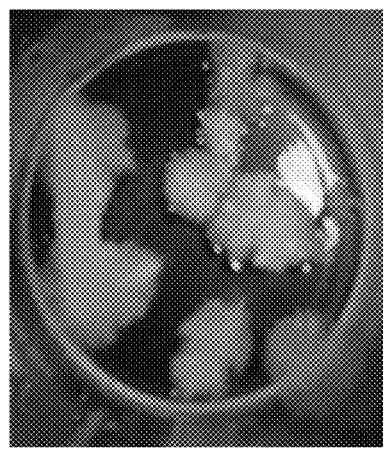

A clear gel solution of $K_7MgCit_2F_3$ was allowed to dry slowly at RT for two months and a macrocrystalline product was formed as shown in FIG. 20 (A is a top view, B is a bottom view, and C is a front view of the beaker).

The word, "a" or "an," when used in conjunction with the term "comprising" in the claims and/or the specification can mean "one," but it is also consistent with the meaning of "one or more," "at least one," and "one or more than one." Still further, the terms "having," "including," and "comprising" are interchangeable and one of skill in the art is cognizant that these terms are open ended terms.

Where the terms, "comprise", "comprises," "comprised," or "comprising," are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms, "comprising" or "comprise(s)" or "comprised," are optionally replaced with terms analogous in grammar, e.g., "consisting/consist(s)," or "consisting essentially of/consist(s) essentially of," to thereby describe further embodiments.

All references throughout this application, for example, patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). The references are incorporated for purposes of enablement and written description.

The invention has been described with reference to various specific and preferred embodiments and techniques. However, it should be understood that many variations and modifications can be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed as if separately set forth. This invention is not to be limited by the embodiments disclosed, including any shown in the drawings or exemplified in the specification, which are given by way of example or illustration and not of limitation. The scope of the invention shall be limited only by the claims.

REFERENCES

Antich, P. P., et al., J. Bone Miner. Res. 1993, 8(3):301-311.
Caverzasio, J. et al., "Fluoride: Mode of Action," 1998, Bone: 22(6) 585-589.
King, N., et al., Biolog. Trace Elem. Res., 1991, 31:223-233.
Koenig, K. et al., J. Urol., 1991, 145:330-334.
Lehmann, R. et al., Bone, 1998, 22:273-278.
Luisi, B. S., et al. ChemComm, Jun. 8, 2007, 2802-2804.
Meunier, P. J. et al., N. Engl. J. Med., 2004, 350:459-68.
Mertz, W. Science, 1981, 213:1332-1338.
Oh, M. and Mirkin, C. A., Nature, Dec. 1, 2005, 438:651-654.
Pak, C. Y., et al., Ann. Intern. Med., 1995, 123:401-408.
Pak, C. Y. et al., J Clin Endocrinol Met., 1989, 68:150-158.
Strause, L. et al., J. Nutr., 1994, 124:1060-1064.
Tang, R., et al., Mater. Res. Soc. Symp. Proc. 2004, 823:81-89.
Vescini, F. et al., J. Endocrinol. Invest., 2005, 28:218-222.
Wikipedia, *Coordination Polymers*, downloaded Jul. 14, 2008.
Zerwekh, J. E., et al. Calcif. Tissue Int., 1997, 61:272-278.
U.S. Pat. No. 5,219,889
U.S. Pat. No. 5,432,200
U.S. Pat. No. 6,287,607
U.S. Pat. No. 7,091,246

The invention claimed is:

1. A compound of the formula: $A_xB_yCit_2F_z$, wherein:
A is a cation selected from the group consisting of the Periodic Table IA metal ions lithium (Li), sodium (Na), and potassium (K) and the Periodic Table IIA metal ions Magnesium (Mg) and Calcium (Ca);
B is a cation selected from the Periodic Table IIA metal ions Magnesium (Mg) and Calcium (Ca), and the Periodic Table divalent d-block transition metal ions Copper (Cu) and Zinc (Zn);
A and B are different;
"Cit" is tribasic citric acid anion;
the ratio of x to y is equal or higher than 1.0 but lower than 8.0;
z is selected such that electroneutrality is preserved; and wherein z is adjusted so that when A and B are both selected from ions having a valence of plus 2, 2x+2y is equal to z+6;
or wherein z is adjusted so that when A is selected from ions having a valence of plus 1 and B is selected from ions having a valence of plus 2, x+2y is equal to z+6; and
wherein said compound comprises fluoride.

2. The compound of claim 1 represented by the formula, $A_xB_yCit_2F_z.mH_2O$, wherein m is 0-12.

3. The compound of claim 1 represented by a formula selected from the group consisting of: $A_3Mg_3(C_6H_5O_7)_2F_3$; $A_6Mg_3(C_6H_5O_7)2F_6$; and $A_7Mg(C_6H_5O_7)_2F_3$; wherein A is potassium or sodium.

4. The compound of claim 1 which is $K_3Mg_3(C_6H_5O_7)_2F_3$ or $K_7Mg(C_6H_5O_7)_2F_3$.

5. A method of preventing dental caries or bone loss comprising administering to a patient in need thereof a composition comprising a compound of claim 1.

* * * * *